(12) United States Patent
Abatangelo et al.

(10) Patent No.: US 6,803,037 B2
(45) Date of Patent: Oct. 12, 2004

(54) HYALURONIC ACID DERIVATIVE BASED CELL CULTURE AND BIODEGRADABLE THREE-DIMENSIONAL MATRIX

(75) Inventors: Giovanni Abatangelo, Saccolongo (IT); Lanfranco Callegaro, Theine (IT)

(73) Assignee: Fidia Advanced Biopolymers S.r.l., Brindisi (IT)

( * ) Notice: Subject to any disclaimer, the term of this patent is extended or adjusted under 35 U.S.C. 154(b) by 0 days.

(21) Appl. No.: 09/445,604

(22) PCT Filed: Jun. 10, 1998

(86) PCT No.: PCT/EP98/03510

§ 371 (c)(1),
(2), (4) Date: Dec. 7, 1999

(87) PCT Pub. No.: WO98/56897

PCT Pub. Date: Dec. 17, 1998

(65) Prior Publication Data

US 2002/0192261 A1 Dec. 19, 2002

(30) Foreign Application Priority Data

Jun. 11, 1997 (IT) .......................... 97A000122

(51) Int. Cl.[7] .......................... A01N 63/00; A61F 13/00; C12N 5/00; C12N 5/06; C12N 5/08
(52) U.S. Cl. ...................... 424/93.7; 424/422; 435/325; 435/347; 435/371; 435/395
(58) Field of Search ................................ 424/422, 423; 435/325, 370, 371

(56) References Cited

U.S. PATENT DOCUMENTS

| | | | | |
|---|---|---|---|---|
| 5,131,907 A | * | 7/1992 | Williams et al. | 600/36 |
| 5,520,916 A | * | 5/1996 | Dorigatti et al. | 424/401 |
| 6,027,741 A | * | 2/2000 | Cialdi et al. | 424/422 |

FOREIGN PATENT DOCUMENTS

| | | |
|---|---|---|
| IT | 0216453 | 4/1987 |
| IT | 0265116 | 4/1988 |
| IT | 0341745 | 11/1989 |
| IT | 9525751 | 9/1995 |
| IT | 9633750 | 10/1996 |
| IT | 9635720 | 11/1996 |
| IT | 9637519 | 11/1996 |
| IT | 9845335 | 10/1998 |
| JP | 529659 | 3/1993 |
| WO | WO 96/33750 | * 10/1996 |
| WO | WO 97/18842 | * 5/1997 |

OTHER PUBLICATIONS

Alberts et.al.; Molecular Biology of the Cell, Third Edition, 1994: 892–893.*
Riddell et. al.; T–Cell mediated rejection of gene–modified HIV–Specific Cytotoxic T limphocytes in HIV–infected patents, 1996, Nature Medicine vol. 2: 216–223.*
Kohn; Gene therapy for haematopietic and lymphoid disorders, 1997, Clin. Exp. Immunol 107: 54–57.*
Verma et al. Nature. 389: 239–242. Sep. 1997.*
Cortivo, R. et al., In vitro Studies on Biocompatibility of Hyaluronic Acid Esters, 1992, Biomateria is vol. 12:727–730.
Denizot, F. et al., Rapid Colorimetric Assay for Cell Growth and Survival, 1986, J. Immun. Methods 89:271–277.
Matta, S.G. et al., Pancreatic Islet Cell Reaggregation Systems, 1994, Pancreas, vol. 9:439–449.
Montesano, R. et al., Basic Fibroblast Growth Factor Induces Angiogenesis In vitro, 1986, Proc. Natl. Acad. Sci. USA vol. 83:7297–7301
Jaffe, E.A. et al., Identification by Morphologic and Immunologic Criteria, 1973, J.Clin.Investigation vol. 52:2745–2756.
Montesano, R., et al., Synergistic Effect of Hyaluronan Oligosaccharides and Vascular Endothelial Growth Factor an Angiogenesis In Vitro, 1996, Laboratory Investigation, vol.52:249.
Folkman, J., et al., Angiogenesis In vitro, 1980, Nature, vol. 288:551.
Folkman, J., et al., Long–term Culture of Capillary Endothelial Cells., 1979, Proc. Natl. Acad. Sci. Use vol. 76:5217–5221.
Madri, J. et al., Capillary Endothelial Cell Cultures: Phenotypic Modulation by Matrix Components, 1983, J. Cell Biol. vol. 97:153–165.
Gerlach, J. et al., Improved Hepatocyte In vitro Maintenance in a Culture Model With Woven Multicompartment Capillary Systems: Electron Microscope Sutdies, 1995, Hepatology vol. 22:546.
Limat, A., et al., Serial Cultivation of Single Keratinocytes from the Outer Root Sheath of Human Scalp Hair Follicles, 1986, J. Investigative Dermatology, vol. 87:485.

* cited by examiner

Primary Examiner—David Guzo
Assistant Examiner—Quang Nguyen
(74) Attorney, Agent, or Firm—Hedman & Costigan, P.C.

(57) ABSTRACT

The present invention relates to a biological material having a matrix which contains at least one derivative of hyaluronic acid on which endothelial cells, glandular cells such as islets of Langerhans and liver cells, skin adnexa, germinative cells of hair bulbs, and kerinatocytes are grown, optionally in presence of a medium treated with fibroblasts or in a co-culture with fibroblasts. A process for the production of said biologic materials and the use of such materials for human and veterinary applications such as cardiovascular and oncological surgery, in connection with transplants, for enhancing the biological process of tissue vascularization and for aesthetic use, and also for the screening of medicaments or toxic substances and as a support in the process of gene transfection. The biological material is based on an efficacious cell culture and a biocompatible and biodegradable three-dimensional matrix containing a hyaluronic acid derivative.

35 Claims, 7 Drawing Sheets

HYALURONIC ACID DERIVATIVE BASED CELL CULTURE AND BIODEGRADABLE THREE-DIMENSIONAL MATRIX

FIELD OF THE INVENTION

The present invention concerns a biological material comprising a matrix consisting of at least one derivative of hyaluronic acid on which endothelial cells, glandular cells such as islets of Langerhans and liver cells, skin adnexa and germinative cells of hair bulbs are grown.

BACKGROUND OF THE INVENTION

It is possible nowadays to reproduce angiogenesis, that is, the formation of new blood vessels, experimentally in vitro by various means and using different stimulants such as Vascular Endothelial Growth Factor (VEGF) or basic Fibroblast Growth Factor (bFGF) (R. Montesano et al., PNAS USA, 1986, 83; 7297–7301, "Basic Fibroblast Growth Factor induces angiogenesis in vitro"; J. Folkman et al., PNAS USA, 1979, 76; 5217–5221, "Long term culture of capillary endothelial cells"; R. Montesano et al., Lab. Invest., 1996, 75; 249–262, "Synergistic effect of hyaluronan oligosaccharides and vascular endothelial growth factor on angiogenesis in vitro").

The reorganization of endothelial cells into tubular structures has been observed, for example, in the presence of collagen in the course of gelation, or between double layers of collagen.

Even more encouraging results have recently been obtained using as a culture support basement membrane extracts (Matrigel), on which the angiogenic mechanism seems more rapid and more easily reproducible. It was thus possible to demonstrate that the presence of a scaffold containing collagen fibers facilitates cell differentiation which, in the case of endothelial cells, translates into the organization of a thin web of tubular structures similar to that found in the extracellular matrix of connective tissues (J. Folkman et al., Nature, 1980, 288, 551–556, Angiogenesis in vitro"; J. A. Madri et al., J. of Cell Biol., 1983, 97, 153165, "Capillary endothelial cell culture: phenotypic modulation by matrix components").

It is well known that matrices of partial or total esters of hyaluronic acid with benzyl alcohol (HYAFF®) in the form of nonwoven fabric are suitable for the in vitro growth and development of various cell types such as fibroblasts (WO 96/33750).

WO 97/18842 refers to a culture of autologous or homologous bone marrow stem cells partially or completely differentiated into cellular lines of a specific connective tissue and the extracellular matrix produced by said connective tissue, said cells growth onto a scaffold of a three-dimensional biocompatible and biodegradable matrix consisting of a hyaluronic acid derivative. The success of this biological material was because the cells used are very active and can be suitably differentiated into various cell lines when placed onto the matrix. From these stem cells it is possible to obtain differentiated cells such as fibroblasts, adipocytes, myoblasts, osteoblasts and chondrocytes.

Weak and fragile differentiated cells such as endothelial, glandular cells, islets of Langerhans, liver cells or skin adnexa are more difficult to be isolated and cultured onto artificial or plastic support than staminal cells and they show poor proliferative properties and short survival times.

For example, liver cells can survive in vitro for about 7 weeks with less than 50% of the cells remaining viable (J. C. Gerlach et al., Hepatology August 1995, Vol. 22 No. 2, pages 546–552), while skin adnexa last about two weeks (A. Limat et al., The Journal of Investigative Dermatology, Vol. 87, No. 4 October 1986, pages 485–488), and islets of Langerhans just a few days (S. G. Matta, Pancreas, Vol. 9, No. 4, 1994, pages 439449).

It therefore follows that although the properties of HYAFF® matrices are already known to favour the growth and development in vitro of resistant and very active cellular elements such as staminal cells or fibroblasts, ecc. an expert in the field would have not be able to predict that satisfactory proliferation rates and survival times can be achieved by cultivating cell types like poor resistant, weak and with short time of survival cells as above said.

SUMMARY OF THE INVENTION

The authors of the present invention have instead surprisingly found that also poor resistant and weak cells such as endothelial cells, glandular cells and skin adnexa, germinative cells of hair bulbs, ecc. can efficiently grow on a hyaluronic acid derivative matrix.

A characteristic of the present invention is, therefore, a biological material comprising:
a) at least one cell type selected from the group consisting of endothelial cells, glandular cells, skin adnexa, germinative cells of hair bulbs and optionally keratinocytes; and
b) a biocompatible and biodegradable three-dimensional matrix comprising at least one hyaluronic acid derivative and optionally collagen and/or fibrin.

The authors of the present invention have furthermore surprisingly found that when the above said cells, comprised in the biological material according to the inventions are cultivated in particular culture conditions such as in presence of a medium treated with fibroblasts or in a co-culture with fibroblasts seeded on the biomaterial, at different times, preferably several days, previously or at the same time as the cells, the proliferation rate is significantly higher than that which is achieved using other supports in the same conditions.

A further aspect of the present invention is therefore a biological material comprising:
a) at least one cell type selected from the group consisting of endothelial cells, glandular cells, skin adnexa, germinative cells of hair bulbs, and optionally keratinocytes cultured in presence of a medium treated with fibroblasts or in a co-culture with fibroblasts; and
b) a biocompatible and biodegradable three-dimensional matrix comprising at least one hyaluronic acid derivative and optionally collagen and/or fibrin.

Another aspect of the present invention is a process for the preparation of a biological material according to the invention.

The invention relates also to the use of the biological material according to the invention for human and veterinary use, in cardiovascolar and oncological surgery, in transplants, to enhance the biological process of tissue vascularization and for aesthetic use.

Furtherly, another aspect is the use of the biological material according to the invention for the screening of medicaments or toxic substances and as a support for gene transfection.

It shows the absorbance values at 534 nm, obtained by MTT assay 24, 72 and 96 hours after seeding of the HUVEC on small circles of nonwoven fabric NW11 in presence of: a) growth factors; and b) culture medium treated with fibroblasts.

Figure 2:
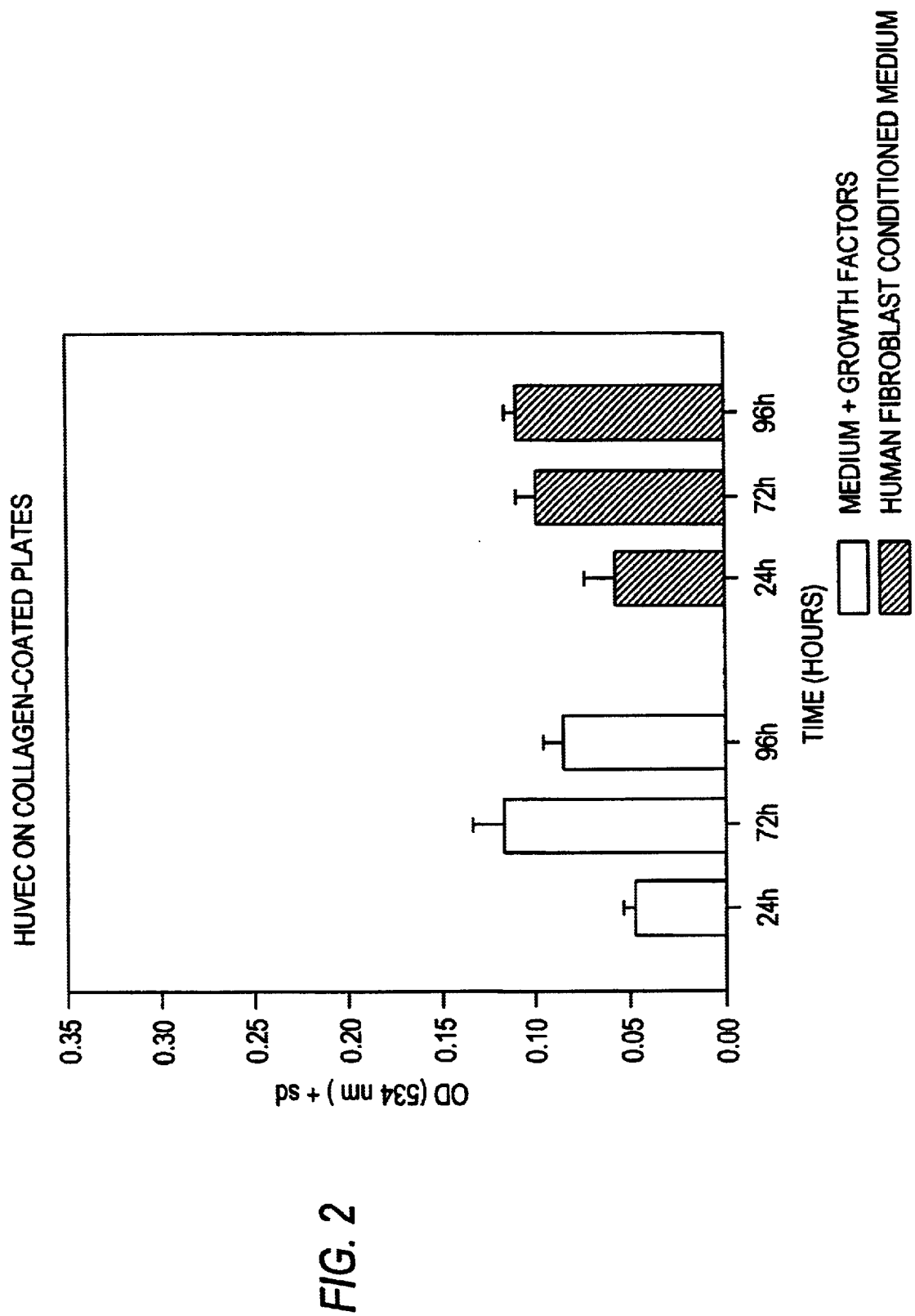

FIG. 2: is a histogram of a MTT test showing the values obtained with cultures of HUVEC on collagen-treated wells with: a) medium complete with growth factors; and b) medium treated with fibroblasts.

Figure 3:
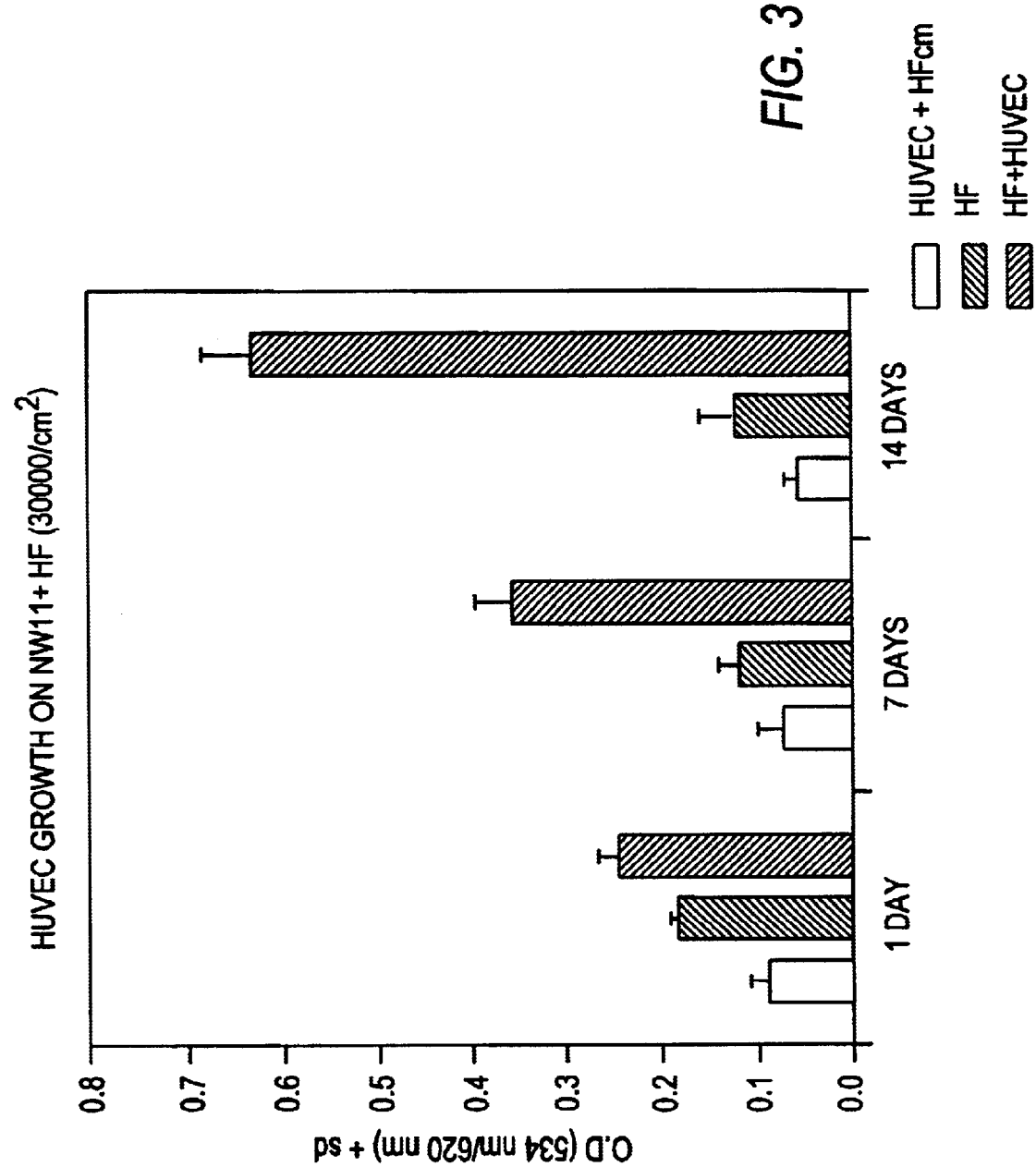

FIG. 3: is a histogram of a MTT test showing the growth rate of HUVEC (30,000/cm$^2$) in the following conditions: a) in medium treated with three-day fibroblast cultures (HFcm+HUVEC); b) fibroblasts (HF) alone; and c) in co-cultures with fibroblasts cultured in quantities of 30,000/cm$^2$ (HF+HUVEC).

The absorbance values are calculated at 534/620 nm. 1, 7 and 14 days are the culture times after seeding of HUVEC onto small circles of nonwoven HYAFF® NW11.

Figure 4:
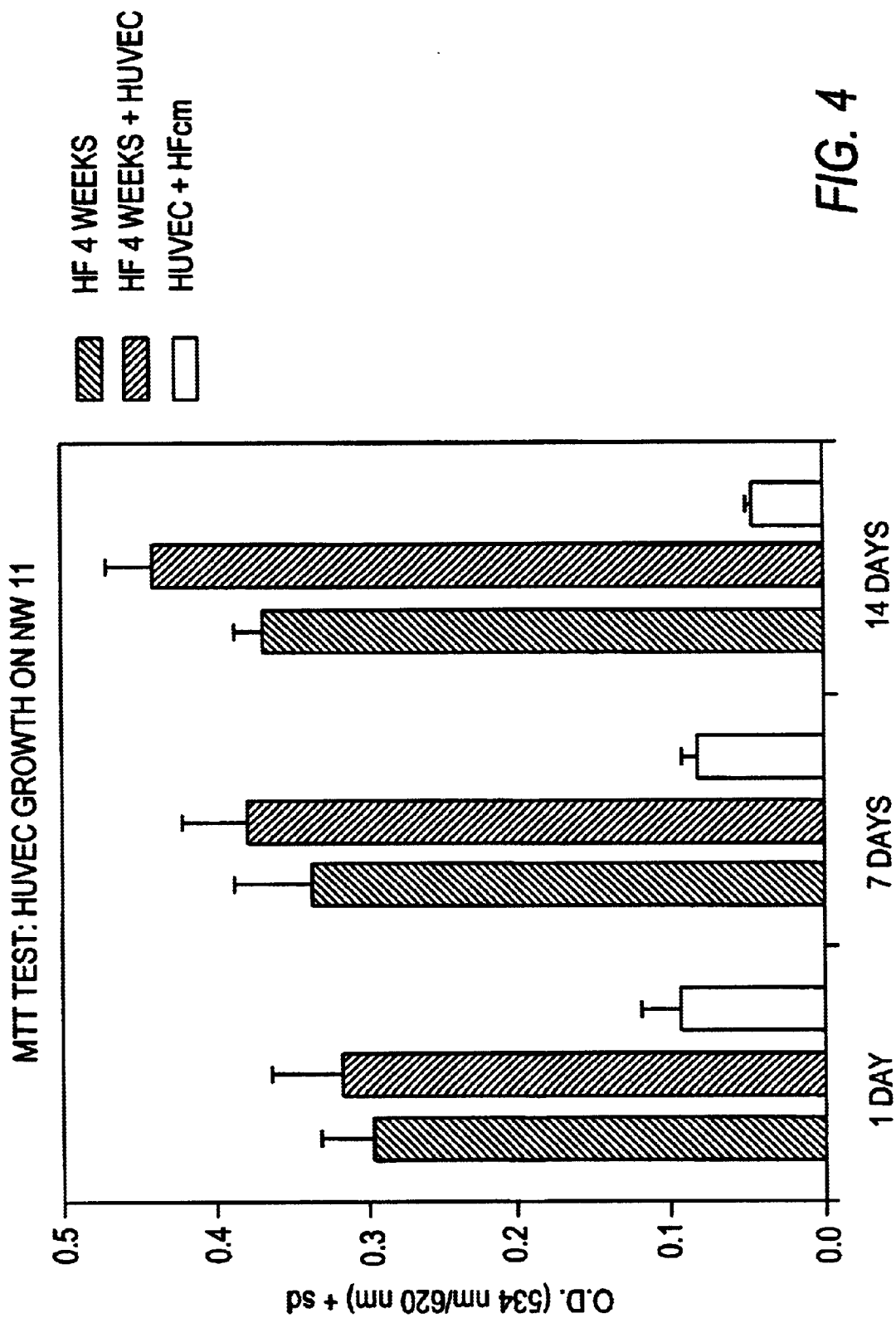

FIG. 4: is a histogram relating to a MTT test and showing the growth rate of HUVEC on HYAFF® NW11 under the conditions of: a) fibroblasts (HF) seeded for 4 weeks; b) fibroblasts (HF) seeded for 4 weeks and HUVEC (HF 4 weeks+HUVEC); and c) HUVEC in medium treated with fibroblast cultures (HFcm+HUVEC).

The absorbance values are calculated at 534/620 nm. 1, 7 and 14 days are the culture times after seeding of HUVEC onto small circles of nonwoven HYAFF® NW11. Fibroblasts are cultivated in great quantities (100,000/cm$^2$).

Figure 5:
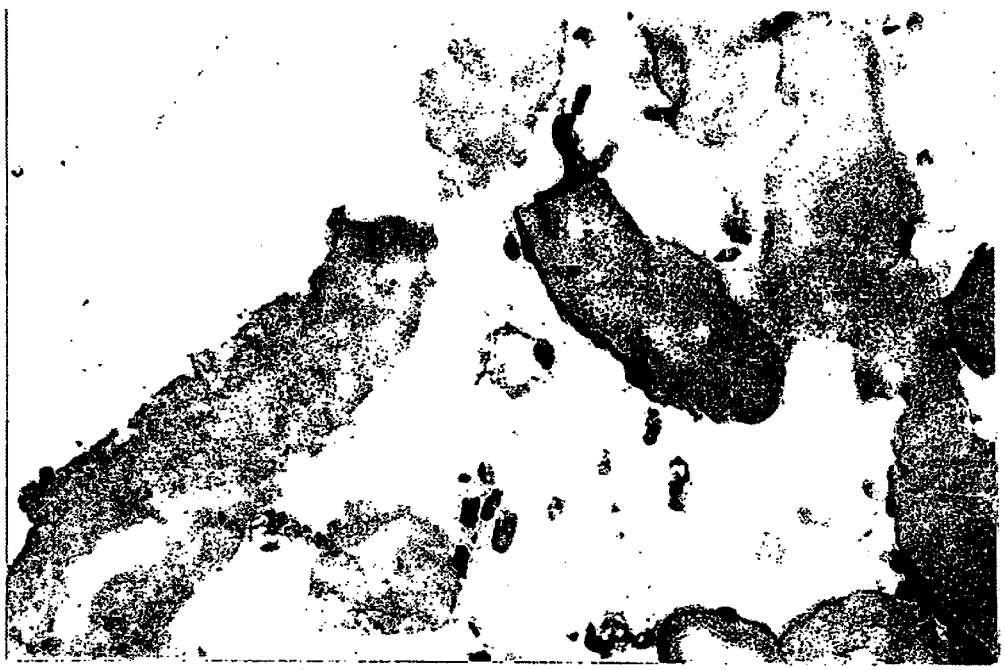

FIG. 5: it shows a cross-section of the matrix of hyaluronic acid total benzyl ester (HYAFF®11) in the form of nonwoven fabric on which HUVEC have been grown in the presence of a 4-week fibroblasts culture. The HUVEC were left in the culture for 14 days. It is possible to note the capillary lumen within a well-organized connective matrix. The hydrated fibers of nonwoven fabric are visible.

Figure 6:

FIG. 6: it shows a cross-section of the matrix of HYAFF®11 in the form of nonwoven fabric on which HUVEC have been grown in the presence of a 4-week fibroblast culture. The HUVEC are left in the culture for 5 days. It is possible to note the tubular structure constituted by the association of endothelial cells, the cell bodies with nuclei raised towards the outside, the lighter-coloured inner lumen surronded by cell bodies.

Figure 7:

FIG. 7: it illustrates the affinity between the cells and the nonwoven fabric of HYAFF®11, as shown by the fiber of nonwoven fabric completely covered in endothelial cells. It is possible to note the nuclei, the cell bodies and the points of contact between the cells are.

Figure 8:

FIG. 8: it shows a cross-section of the matrix of HYAFF®11 in the form of a nonwoven fabric on which HUVEC have been grown in the presence of a 4-week fibroblast culture. The HUVEC were left in the culture for 14 days. It is possible to note the fibroblast-rich matrix spread over the surface under a hair-like structure where a cell with different morphology (HUVEC) is folded over itself.

Figure 9:

FIG. 9: Endothelial cells were seeded and grown together with fibroblasts. The photograph refers to a 6 days of culture and shows clusters of endothelial cells in the vicinity of a fiber of nonwoven fabric on which the fibroblasts have deposited the extracellular matrix. Underneath the fiber in the foreground it is possible to see an endothelial cell folded over itself.

DETAILED DESCRIPTION OF THE INVENTION

The hyaluronic acid derivatives constituting the three-dimensional matrix of the biological material according to the present invention are chosen from the group consisting of:

hyaluronic acid esters wherein part or all of the carboxy functions are esterified with alcohols of the aliphatic, aromatic, arylaliphatic, cycloaliphatic, heterocyclic series (EP 0216453 B1);

autocrosslinked hyaluronic acid esters wherein part or all of the carboxy groups are esterified with the alcoholic functions of the same polysaccharide chain or other chains (EP 0341745 B1);

crosslinked compounds of hyaluronic acid wherein part or all of the carboxy groups are esterified with polyalcohols of the aliphatic, aromatic, arylaliphatic, cycloaliphatic, heterocyclic series, generating crosslinking by means of spacer chains (EP 0265116 B1);

hemiesters of succinic acid or heavy metal salts of the hemiester of succinic acid with hyaluronic acid or partial or total esters of hyaluronic acid (WO 961357207);

sulphated hyaluronic acid (WO 95/25751) or N-sulphated hyaluronic acid (PCT Appln. No. PCT/EP98/01973 filed on Apr. 3, 1998) and the derivatives thereof;

hyaluronic acid ester as above which is a benzyl ester with a degree of esterification of between 25% and 100%; and nonwoven HYAFF® matrix (U.S. Pat. No. 5,520,910).

The above hyaluronic acid derivatives can also be used alone or in association with one another.

The biocompatible, three-dimensional matrix can be used in the form of a nonwoven fabric, sponges, granules, microspheres, membranes, films, guide channels and gauzes, and associations of the same.

The preparation of said nonwoven fabric constituted by the hyaluronic acid derivative and in particular by the hyaluronic acid ester is described in the US patent application by the Applicant U.S. Pat. No. 5,520,916.

The biological material according to the invention comprises a matrix consisting of at least one hyaluronic derivative and optionally collagen and/or fibrin onto which the cells will be cultured, and at least one cell type selected from weak and fragile differentiated cells. Such cells are more difficult to be isolated and cultured onto synthetic, artificial or plastic support than staminal cells and they normally show poor proliferative properties and short survival times. Surprisingly, when these cells are grown onto the matrix according to the invention they shown high proliferative rate and longer survival times.

The cells according to the invention are selected from the group consisting of endothelial cells, glandular cells, skin adnexa, germinative cells of hair bulbs and optionally keratinocytes.

Endothelial cells are preferably taken from umbilical vein or from dermis or other tissue wherein blood vessels are present.

Glandular cells are preferably liver cells or langerhans cells.

Skin adnexa are preferably sebaceous glands or sweat glands.

Hair bulbs and germinative cells are preferably taken from autologous, homologous or heterologous hair bulbs.

It has been observed, surprisingly, that when said cells grown on matrices constituted by hyaluronic acid derivatives, optionally in the presence of fibrin and/or collagen, supplemented with medium treated with fibroblasts and in co-culture with fibroblasts seeded on the biologic material according to the invention, preferably several days previously or at the same time as the cells, the proliferation rate is significantly higher and the survival times are longer than in absence of fibroblasts. The results were also higher than on collagen in the same culture conditions.

The medium treated with fibroblasts is obtained culturing fibroblasts onto the matrix of hyaluronic acid derivative, immersed in the culturing medium (liquid comprising the substances useful for the growth of fibroblasts). Medium treated with fibroblasts, therefore, consists of a culture medium comprising the substances secreted by fibroblasts which is then taken and utilized in the cultures of cells (according to the invention) on another matrix of hyaluronic acid derivative. According to a particular realisation of the present invention, human endothelial cells are extracted from the umbilical vein (HUVEC) by enzymatic digestion with collagenase (E. A. Jaffe, J. Clin. Invest., 1973, 52, 2745–2756, "Culture of human endothelial cells derived from umbilical veins") or from homologous, autologous or heterologous dermal tissue, or from other types of tissue containing vascular tissue and preferably seeded and left to proliferate on nonwoven HYAFF® matrices (U.S. Pat. No. 5,520,910). Matrices of HYAFF® facilitate the growth of cells in all three spatial dimensions, as they can arrange themselves in tubular structures. The biological material thus constituted can be used to advantage in skin transplants, where the endothelial cells favour the neovascularization of the transplanted tissue which would otherwise take much longer due to the migration of endothelial elements from the area surrounding the transplant, thus jeopardizing the very survival of the new tissue.

Another advantage of speedy vascularization of a skin substitute transplanted on a skin lesion is that previously prepared strips of keratinocytes can be applied immediately, or almost immediately, without the risk of the cells undergoing necrosis due to lack of nourishment.

Besides being used in skin transplants, the biological material according to the invention comprising endothelial cells may be used on burns or traumas, in oncology and other fields of surgery such as cardiovascular and aesthetic surgery, to favour the biological process of vascularization of the tissues.

Glandular elements such as liver cells, islets of Langerhans and skin adnexa grown on matrix according to the present invention show longer survival times. It therefore follows that a biological material wherein the glandular elements are liver cells can be used to advantage as a viable hepatic tissue to be transplanted in cases of severe liver insufficiency.

A biological material wherein the glandular elements are represented by islets of Langerhans can be advantageously inserted into the human organism, for instance subcutaneously or into the pancreatic parenchyme, in cases of deficient insulin production.

A biological material comprising a biodegradable, biocompatible, threedimensional matrix constituted by at least one hyaluronic acid derivative and by a culture of skin adnexa such as hair bulbs, sebaceous glands, sweat glands and germinative cells of hair bulbs preferably grown in medium conditioned with fibroblasts or in co-culture with fibroblasts, can be used to advantage in scalp and skin transplants together with endothelial cells, and possibly with keratinocytes, thus obtaining a tissue very similar to human skin.

Lastly, it has been seen that the germinative cells in hair bulbs in the same culture conditions give rise to new hair elements.

The biological material according to the invention can be prepared according to the following process comprising the following steps:

i) isolating cells selected from the group consisting of endothelial cells, glandular cells, skin adnexa, germinative cells of hair bulbs, and optionally keratinocytes;
ii) preparing a biocompatible and biodegradable three-dimensional matrix comprising at least one hyaluronic acid derivative and optionally collagen and/or fibrin;
iii) seeding at least one type of said cells on said matrix optionally in presence of a medium treated with fibroblasts or in a co-culture with fibroblasts.

According to a particular realisation of the invention the process comprises the following steps:
i) isolating endothelial cells from human umbilical vein by enzymatic digestion with collagenase;
ii) amplification on collagen-treated dishes;
iii) preparing a biocompatible and biodegradable three-dimensional matrix comprising at least one hyaluronic acid derivative and optionally collagen and/or fibrin;
iv) seeding said cells, and optionally other cells according to the invention, on said matrix optionally in presence of a medium treated with human fibroblasts in primary culture or in a co-culture with human dermal fibroblasts.

The invention relates also to the use of the biological material according to the invention for human and veterinary use, in cardiovascolar and oncological surgery, in transplants, to enhance the biological process of tissue vascularization and for aesthetic use.

Lastly, the biological materials according to the present invention can be used in the screening of medicaments or toxic substances and as supports for gene transfection.

The biologic material according to the present invention can be used as alternative to the animal experiment method for testing the pharmacologic substances, for instance, in order to evaluate the toxicity of a substance or for testing the efficiency of biomedical devices such as, for example, the influence of magnetic field.

The biological material according to the present invention can also be used as a support for genetic transfection.

Genetic transfection is applied, in genetic therapy, by transplanting genetically modified cells. Human cells are cultivated in vitro and transfected with a gene coding for a specific amino acid sequence useful against the pathology to treat and then such treated cells are re-implanted onto human body.

In the application of the genetic therapy there is often the problem connected to the fact that cells re-implanted in the same organism do not remain in situ long enough in order to express their action. Culturing the cells on matrix according to the present invention is possible to obtain high proliferation rate and engineered tissues having a complex structure very similar to that of the natural tissue of the organism and they are able to give an efficient surgical workability and can be re-implanted overcoming the problem connected to the cells dispersion.

For purely descriptive purpose, the present invention will be furtherly described according to the following Examples.

EXAMPLE 1

Extraction of Endothelial Cells from the Umbilical Vein

Endothelial cells (HUVEC) were taken from the umbilical vein by gently cannulating it with a thick, sterile needle, being careful not to damage the walls. The vessel is then rinsed with saline solution (phosphate buffer without $Ca^{++}$ and $Mg^{++}$, PBS--) so as to eliminate any residue blood. The cells were detached from the walls of the vessel by perfusion with a solution of collagenase (1 mg/ml, 300–400 U/mg), and immersion in saline solution at 37° C. for 5 minutes.

The reaction is stopped with complete medium (M199 1×+20% foetal calf serum+L-Glutamine 2 mM+Penicillin/Streptomycin (100 U/ml)/(100_g/ml)+Fungizone 2.5 æg/ml).

Following centrifugation, the cell sediment is re-suspended in complete medium and seeded in a cell culture flask previously treated with a solution of collagen I (10 µg/ml) in PBS-, overnight at 37° C.

Once they have reached confluence, the HUVEC are removed from the culture dish with trypsin 0.05%-EDTA 0.02% and amplified with their own medium supplemented with hECGF (0.1 ng/lml) and Heparin (100 µg/ml) and bFGF (10 ng/ml).

EXAMPLES 2–5

Comparison of the Growth of Endothelial Cells in Different Culture Conditions

EXAMPLE 2

Human umbilical vein endothelial cells (HUVEC) are first amplified on gelatin-treated dishes and then seeded on membranes of nonwoven fabric (HYAFF®) in 24-well dishes at a density of 30,000/cm2 in different culture conditions:
1) with a medium enriched with growth factors (M199 complete with 20% foetal calf serum), bFGF at a concentration of 10 ng/ml, heparin at a concentration of 100 ng/ml and ECGF at a concentration of 0.1 ng/ml;
2) with a medium treated with human fibroblasts three days before seeding (HUVEC +HFcm);

Cell proliferation was indirectly assessed at various time intervals by MTT assay (F. Denizot, J. Immunol. Met., 1986, 89, 271–277, "Rapid calorimetric assay for cell growth and survival"). Each specimen was set up in triplicate.

Figure 1:
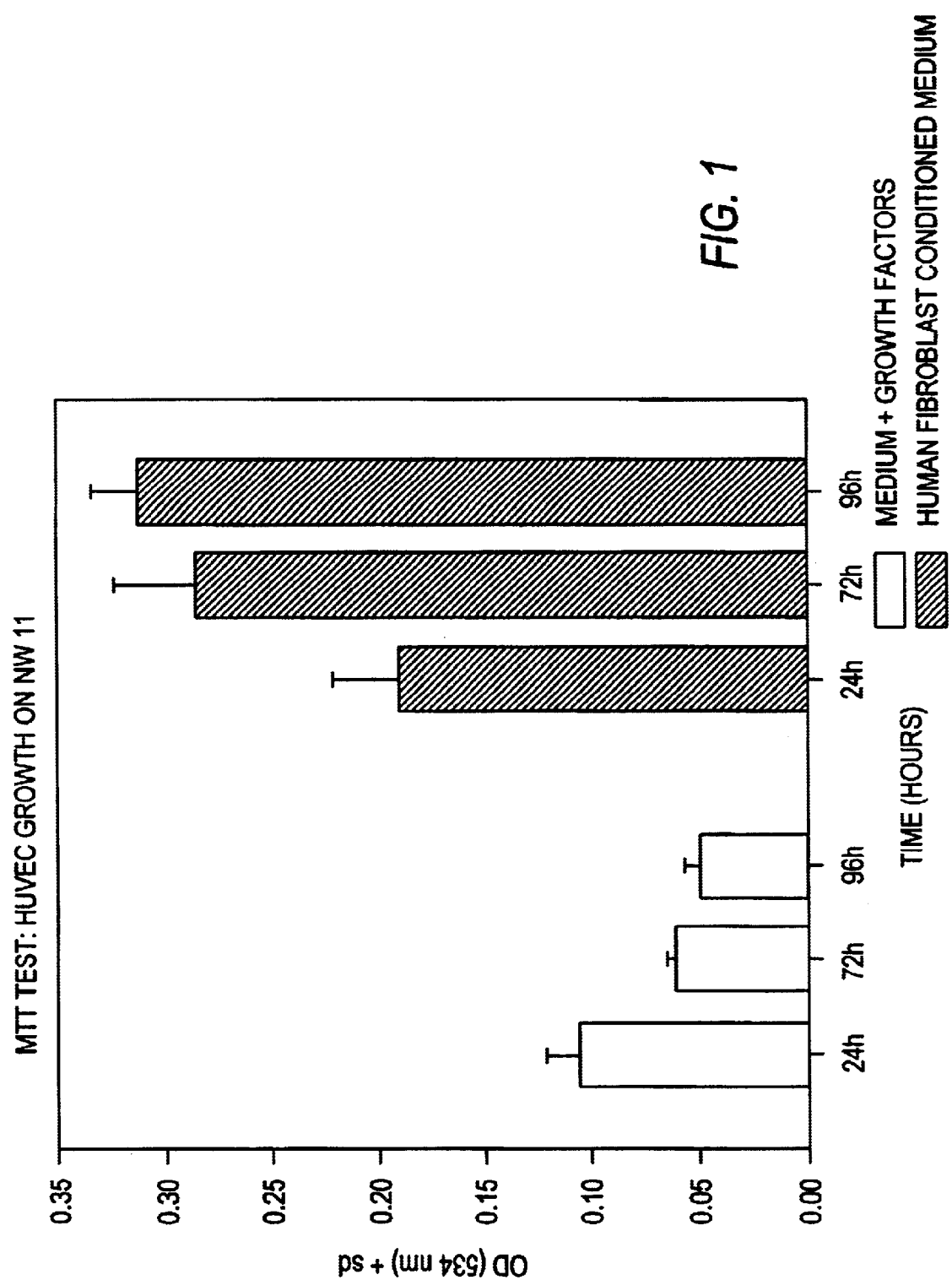
FIG. 1: is a histogram of a MTT test, which relates to the growth of Human vein umbilical vein endothelial cells (HUVEC) on a hyaluronic acid derivative NW11.

Results, reported in FIG. 1, show the absorbance values at 534 nm, obtained by MTT assay 24, 72 and 96 hours after seeding of the HUVEC on small circles of nonwoven fabric of HYAFF®11 (NW11) in the presence of growth factors and culture medium treated with fibroblasts. The graph shows that, over a period of 96 hours, the culture medium supplemented with growth factors normally used to grow these cell in vitro is not sufficient to support cell growth on biomaterial made of HYAFF®11.

The rate of cell proliferation increases, however, when medium treated with a three-day growth of primary fibroblasts is added to the culture medium.

EXAMPLE 3

HUVEC were cultured like in Example 2, but on collagen-coated plates instead of a support of HYAFF®.

Results, reported in FIG. 2, show the values obtained with cultures of endothelial cells on collagen-treated wells with medium complete with growth factors and medium treated with fibroblasts. MTT assay showed that although the proliferation rate was similar in the two types of well, it was notably lower than the growth values obtained with the samples of nonwoven HYAFF®11 supplemented with fibroblast-treated medium (see FIG. 1).

EXAMPLE 4

HUVEC were cultured on NW11 like in the previous examples in presence of human fibroblasts (HF) in the following conditions:
1) in medium treated with three-day fibroblast cultures (HUVEC+HFcm);
2) in presence of HF only;
3) in simultaneous co-cultures with fibroblasts cultured in quantities of 30,000/cm2 (HF+HUVEC).

Results, reported in FIG. 3, show absorbance values at 534/620 nm, after MTT assay, 1, 7 and 14 days after seeding the HUVEC onto small circles of nonwoven HYAFF® in the different conditions described above. It can be seen that the HUVEC in co-culture with fibroblasts (HF+HUVEC) present an increasing growth rate over longer culture times (14 days). The growth rate of HUVEC on nonwoven HYAFF® supplemented with fibroblast treated medium (HUVEC+HFcm) rises over the first few days in culture and then remains steady at around the same values, thus permitting good cell survival.

EXAMPLE 5

HUVEC were cultured like in the previous examples, in the following conditions:
1) in presence of HF only for 4 weeks (HF 4 weeks);
2) in simultaneous co-cultures with human fibroblasts (in quantities of 100,000/cm$^2$) seeded onto the biomaterial 4 weeks before the endothelial cells (HF 4 weeks+ HUVEC);
3) in medium treated with three-day fibroblast cultures (HUVEC+HFcm).

Results, reported in FIG. 4, show the growth rate of the endothelial cells in the different conditions, reported above.

Discussion of Results of Example 2–5

The above data clearly show that the proliferation of endothelial cells on the HYAFF® biomaterial is notably enhanced by the presence of fibroblasts or the addition of medium obtained from the same. The presence of a three-dimensional structure such as that of nonwoven HYAFF® facilitates their growth, as the cells can colonize the web of fibers in all three spatial dimensions. In these conditions it is therefore possible to maintain the cells in culture for over 96 hours, up to a maximum of three weeks, when the fibers of the biomaterial reach a very high level of hydration.

The importance of a web to support cell proliferation has been clearly confirmed by comparing the data with that obtained on gelatin-treated wells, where, in the absence of a three-dimensional structure, the growth of HUVEC is notably limited as they can only proliferate two dimensionally.

It is thus demonstrated that the biomaterials constituted by hyaluronic acid esters in the form of a nonwoven fabric represent a sublayer suitable for the growth and differentiation of HUVEC too. On these scaffolds, such cells are able to proliferate far better than they do on conventional medium. Moreover, there is a very marked difference in the proliferation rates of the cells cultivated in gelatin-treated wells and those cultivated on the biomaterial in question, and this difference is undoubtedly even more significant on the nonwoven HYAFF® fabric in the presence of fibroblasts.

EXAMPLE 6

Liver Cell Isolation and Culture

Liver cells were isolated from the portal vein and hepatic artery of pig's liver by the technique of collagenase perfusion according to Gerlach J. et al., Hepatology, August 1995, pages 546–552.

After an initial amplification on gelatin-treated dishes, the liver cells were seeded in 24-well dishes at a density of 30,000/cm2 in the following culture conditions:
1) on nonwoven HYAFF® in the presence of a medium treated with three-day human fibroblast culture;
2) on nonwoven HYAFF® in a co-culture with human dermal fibroblasts seeded onto the biomaterial;
3) on nonwoven HYAFF® in a co-culture with human dermal fibroblasts seeded onto the biomaterial 7 days before the liver cells;

4) on collagen-treated wells in co-culture with human dermal fibroblasts seeded onto the biomaterial 7 days before the liver cells.

The percentage of viable cells was assessed by two discrete methods:
A) assessment of the morphological characteristics;
Trypan-blue exclusion test.

Cells which became stained and those presenting cytoplasmatic vacuolation, an accumulation of lipid droplets and cytoplasmatic fragmentation were considered to be non-viable.

Each specimen was set up in triplicate.

| % live cells | 1 day | 2 weeks | 4 weeks | 6 weeks | 8 weeks |
|---|---|---|---|---|---|
| 1 | 80 | 25 | 5 | / | / |
| 2 | 80 | 40 | 20 | 5 | / |
| 3 | 90 | 85 | 75 | 60 | 50 |
| 4 | 89 | 83 | 65 | 30 | / |

EXAMPLE 7

Isolation and Culture of Islets of Langerhans

Islets of Langerhans were isolated from rat pancreas by enzymatic digestion with collagenase according to Matta S. G. et al.; Pancreas, Vol. 9, No. 4, 1994.

Following initial amplification on gelatin-treated dishes, the islets of Langerhans were seeded onto nonwoven membranes in 24-well dishes at a density of 30,000/cm2 in different culture conditions:
1) in the presence of a medium treated with a three-day human fibroblast culture;
2) in a co-culture with human dermal fibroblasts seeded on the biomaterial;
3) in a co-culture with human dermal fibroblasts seeded onto the biomaterial 7 days before the islets of Langerhans.

The percentage of live cells was assessed by two discrete methods:
A) assessment of morphological characteristics;
B) Trypan-blue exclusion test.

Cells which became stained and those which presented cytoplasmatic vacuolation, an accumulation of lipid droplets and cytoplasmatic fragmentation were considered to be non-viable.

Each specimen was set up in triplicate.

| % live cells | 1 day | 10 days | 20 days | 30 days | 40 days |
|---|---|---|---|---|---|
| 1 | 90 | 20 | / | / | / |
| 2 | 90 | 40 | 10 | / | / |
| 3 | 90 | 80 | 70 | 55 | 40 |

EXAMPLE 8

Isolation and Culture of Skin Adnexa

Hair bulbs were isolated from fragments of scalp by means of small pincers and scissors under a dissection microscope.

Sebaceous and sweat glands were isolated from fragments of skin obtained during surgery. They were removed by exerting pressure on the skin, thus causing these structures to protrude.

Following an initial amplification on gelatin-treated dishes, the skin adnexa were seeded onto membranes of nonwoven fabric in 24-well dishes at a density of 30,000/cm2 in discrete culture conditions:

1) in the presence of a medium treated with a three-day culture of human fibroblasts;
2) in a co-culture with human skin fibroblasts seeded on the biomaterial 3 weeks before the skin adnexa;
3) in a co-culture with human skin fibroblasts seeded on the biomaterial 5 weeks before the skin adnexa.

Each specimen was set up in triplicate.

The skin adnexa in culture conditions A proved able to survive for about 2–3 days, as assessed by histological investigation.

After this time the glands began to disintegrate, becoming fragmented into non-viable cell groups.

In conditions 2 and 3 the skin adnexa remained integral in the culture for a period of up to 35 days.

Subsequently, they underwent a process of gradual disgregation and finally disappeared.

What is claimed is:

1. A biological material comprising:
   a) at least one autologous or homologous cellular line selected from the group consisting of endothelial cells, glandular cells, skin adnexa and germinative cells of hair bulbs,
   b) a biocompatible and biodegradable three-dimensional matrix, on which said cellular line is seeded and grown, said matrix comprising a hyaluronic acid derivative selected from the group consisting of:
      A) an ester of hyaluronic acid wherein part or all of the carboxylic groups of said hyaluronic acid are esterified with an alcohol of aliphatic, aromatic, arylaliphatic, cycloaliphatic series;
      B) an autocrosslinked ester of hyaluronic acid wherein part or all of the carboxylic moieties of said hyaluronic acid are esterified with the alcoholic groups of the same or a different hyaluronic acid chain;
      C) a hemiester of succinic acid or a heavy metal salt of the hemiester of succinic acid with hyaluronic acid or with a hyaluronic acid ester having part or all of the carboxy groups of hyaluronic acid esterified with an alcohol of aliphatic, aromatic, arylaliphatic, cycloaliphatic series; and
      D) an O-, an N-sulphated hyaluronic acid and a derivative thereof,
   c) optionally collagen and/or fibrin
   d) optionally autologous or homologous keratinocytes
      said autologous or homologous cellular line is cultivated in presence of a medium treated with autologous or homologous human fibroblasts or in a coculture with autologous or homologous human fibroblasts.

2. The biological material according to claim 1 further containing keratinocytes, fibrin and collagen.

3. The biological material according to claim 1, wherein said endothelial cells are isolated from the umbilical vein from dermis or other tissue wherein blood vessels are present.

4. The biological material according to claim 1 wherein the glandular cells are liver or Langerhans' islet cells.

5. The biological material according to claim 1 wherein the skin adnexa are sebaceous glands, sweat glands or hair bulbs and the germinative cells are isolated from autologous or homologous hair bulbs.

6. The biological material according to claim 1, wherein the hyaluronic acid ester is a benzyl ester with a degree of esterification of between 25 and 100%.

7. The biological material according to claim 1, wherein component (b) is in the form of a non woven fabric, sponges, granules, gauzes, microspheres guide-channels or combination with one another.

8. The biological material according to claim 7 wherein component (b) is in the form of a non woven fabric.

9. A process for preparing a biological material according to claim 1 comprising the following steps:

i) isolating at least one autologous or homologous cellular line selected from the group consisting of endothelial cells, glandular cells, skin adnexa, and germinative cells of hair bulbs, ii) preparing a biocompatible and biodegradable three-dimensional matrix, comprising at least one hyaluronic acid derivative and optionally fibrin and/or collagen, and iii) seeding said cellular line on said matrix in the presence of a medium treated with autologous or homologous human fibroblasts or in a co-culture with autologous or homolgous human fibroblasts.

10. The process according to claim 9 wherein, when in step (i) the cellular line is selected from the group consisting of autologous or homologous skin adnexa and germinative cells of hair bulbs, the cellular line is optionally seeded in association with autologous or homologous keratinocytes.

11. A process for the preparation of the biological material according to claim 3 comprising the following steps:

i) isolating endothelial cells from human umbilical vein by enzymatic digestion with collagenase;

ii) amplifying said cells on collagen treated dishes, iii) preparing a biocompatible and biodegradable three-dimensional matrix, comprising at least one hyaluronic acid derivative and optionally fibrin and/or collagen, and iv) seeding said endothelial cells in association with a cellular line selected from the group consisting of glandular cells, skin adnexa and germinative cells of hair bulb in the presence of a medium treated with autologous or homologous human fibroblasts in primary culture or in a coculture with autologous or homologous human fibroblasts.

12. The biological material according to claim 1, for use in human and veterinary surgery.

13. The biological material according to claim 1 wherein component (a) comprises skin adnexa optionally in association with keratinocytes for use in skin transplants.

14. The biological material according to claim 13 wherein component (a) further comprises autologous or homologous endothelial cells facilitating the mechanism of neovascularization of the transplanted skin.

15. The biological material according to claim 1 wherein component (a) comprises germinative cells of hair bulbs for use in scalp transplants.

16. The biological material according to claim 1, wherein component (a) comprises islets of Langerhans for use in case of insufficient insulin production.

17. The biological material according to claim 1, wherein component (a) comprises endothelial cells for use in surgery.

18. The biological material according to claim 17, for use in cardiovascular, aesthetic and oncological surgery.

19. The biological material according to claim 18 for use in surgery to enhance the biological process of tissue vascularisation.

20. The biological material according to claim 1, wherein component (a) is an autologous cellular line as support for gene transfection.

21. The biological material according to claim 1, wherein component (a) is an autologous cellular line for use in gene transfection.

22. An in vitro biological material comprising:

a) at least one cellular line selected from the group consisting of endothelial cells, glandular cells, skin adnexa and germinative cells of hair bulbs, b) a biocompatible and biodegradable three-dimensional matrix, on which said cellular line is seeded and grown, said matrix comprising a hyaluronic acid derivative selected from the group consisting of:

A) an ester of hyaluronic acid wherein part or all of the carboxylic groups of said hyaluronic acid are esterified with alcohols of the aliphatic, aromatic, arylaliphatic, cycloaliphatic series, B) an autocrosslinked ester of hyaluronic acid wherein part or all of the carboxylic moieties of said hyaluronic acid are esterified with the alcoholic groups of the same or a different hyaluronic acid chain, C) a hemiester of succinic acid or a heavy metal salt of the hemiester of succinic acid with hyaluronic acid or with a hyaluronic acid ester having part or all of the carboxy groups esterified with an alcohol of aliphatic, aromatic, arylaliphatic, cycloaliphatic series and D) an O-, an N-sulphated hyaluronic acid and a derivative thereof, c) optionally collagen and/or fibrin d) autologous and/or homologous keratinocytes, said cellular line being cultivated in presence of a medium treated with autologous or homologous human fibroblasts or in a coculture with autologous or homologous human fibroblasts.

23. The biological material according to claim 22, containing autologous or homologous keratinocytes, collagen and/or fibrin.

24. The biological material according to claim 22, wherein said endothelial cells are isolated from the umbilical vein from dermis or other tissue wherein blood vessels are present.

25. The biological material according to claim 22, wherein the glandular cells are liver or Langerhans' islet cells.

26. The biological material according to claim 22, wherein the skin adnexa are sebaceous glands, sweat glands or hair bulbs and germinative cells are isolated from autologous, homologous and heterologous hair bulbs.

27. The biological material according to claim 22, wherein the hyaluronic acid ester is a benzyl ester with a degree of esterification of between 25 and 100%.

28. The biological material according to claim 22, wherein component (b) is in the form of a non woven fabric, sponges, granules, gauzes, microspheres, guide channels or combination with one another.

29. The biological material according to claim 22 wherein component (b) is in the form of a non woven fabric.

30. A process for preparing a biological material according to claim 22 comprising the following steps:

i) isolating at least one cellular line selected from the group consisting of endothelial cells, glandular cells, skin adnexa, and germinative cells of hair bulbs, ii) preparing a biocompatible and biodegradable three-dimensional matrix, comprising at least one hyaluronic acid derivative and optionally fibrin and/or collagen, and iii) seeding said cellular line on said matrix in the presence of a medium treated with autologous or homologous human fibroblasts or in a co-culture with autologous or homolgous human fibroblasts.

31. The process according to claim 30 wherein, when in step (i) the cellular line is selected from the group consisting of skin adnexa and germinative cells of hair bulbs, the cellular line is optionally seeded in association with keratinocytes.

32. A process for preparing the biological material according to claim 24 comprising:
   i) isolating said endothelial cells from human umbilical vein by enzymatic digestion with collagenase;
   ii) amplifying said cells on collagen treated dishes,
   iii) preparing a biocompatible and biodegradable three-dimensional matrix, comprising at least one hyaluronic acid derivative and optionally fibrin and/or collagen, and
   iv) seeding said endothelial cells optionally in association with a cellular line selected from the group consisting of glandular cells, skin adnexa and germinative cells of hair bulb and in the presence of a medium treated with autologous or homologous human fibroblasts in primary culture or in a coculture with autologous or homologous human fibroblasts.

33. The biological material according to claim 22 for the screening of medicaments or toxic substances.

34. A biological material comprising:
   a) at least one autologous or homologous cellular line selected from the group consisting of endothelial cells, glandular cells, skin adnexa and germinative cells of hair bulbs,
   b) a biocompatible and biodegradable three-dimensional matrix, on which said cellular line is seeded and grown, said matrix comprising a hyaluronic acid derivative selected from the group consisting of:
   A) an ester of hyaluronic acid wherein part or all of the carboxylic groups of said hyaluronic acid are esterified with alcohols of the aliphatic, aromatic, arylaliphatic, cycloaliphatic series;
   B) an autocrosslinked ester of hyaluronic acid wherein part or all of the carboxylic moieties of said hyaluronic acid are esterified with the alcoholic groups of the same or a different hyaluronic acid chain; and
   C) a hemiester of succinic acid or a heavy metal salt of the hemiester of succinic acid with hyaluronic acid or with a hyaluronic acid ester having part or all of the carboxy groups of hyaluronic acid esterified with an alcohol of aliphatic, aromatic, arylaliphatic, cycloaliphatic series,
   c) optionally collagen and/or fibrin
   d) optionally autologous or homologous keratinocytes said autologous or homologous cellular line is cultivated in presence of a medium treated with autologous or homologous fibroblasts human or in a coculture with autologous or autologous human fibroblasts.

35. A biological material comprising:
   a) at least one autologous or homologous cellular line selected from the group consisting of endothelial cells, glandular cells, skin adnexa and germinative cells of hair bulbs,
   b) a biocompatible three-dimensional matrix, on which said cellular line is seeded and grown, said matrix comprising an ester of hyaluronic acid wherein part or all of the carboxylic groups of said hyaluronic acid are esterified with alcohols of the aliphatic, aromatic, arylaliphatic, cycloaliphatic series,
   c) optionally collagen and/or fibrin
   d) optionally autologous or homologous keratinocytes said cellular line being cultivated in presence of a medium treated with autologous or homologous human fibroblasts or in a coculture with autologous or homologous human fibroblasts.

* * * * *